United States Patent
Zhang et al.

(10) Patent No.: US 9,243,009 B2
(45) Date of Patent: Jan. 26, 2016

(54) PHOSPHATE ESTER COMPOUND OF HYDROXY ACID SUBSTITUTED PHENOL ESTER, PREPARATION METHOD AND MEDICAL USE THEREOF

(75) Inventors: Wensheng Zhang, Sichuan (CN); Jun Yang, Sichuan (CN); Jin Liu, Sichuan (CN)

(73) Assignees: West China Hospital, Sichuan University, Sichuan (CN); Yichang Humanwell Pharmaceutical Co., Ltd., Yichang (CN)

( * ) Notice: Subject to any disclaimer, the term of this patent is extended or adjusted under 35 U.S.C. 154(b) by 371 days.

(21) Appl. No.: 13/702,204

(22) PCT Filed: Oct. 13, 2010

(86) PCT No.: PCT/CN2010/001601
§ 371 (c)(1),
(2), (4) Date: Dec. 5, 2012

(87) PCT Pub. No.: WO2011/106268
PCT Pub. Date: Dec. 29, 2011

(65) Prior Publication Data
US 2013/0085120 A1    Apr. 4, 2013

(30) Foreign Application Priority Data
Jun. 23, 2010 (CN) .......................... 2010 1 0206942

(51) Int. Cl.
C07F 9/09    (2006.01)
(52) U.S. Cl.
CPC .. *C07F 9/09* (2013.01); *C07F 9/091* (2013.01)
(58) Field of Classification Search
CPC ....................................................... C07F 9/09
See application file for complete search history.

(56) References Cited

U.S. PATENT DOCUMENTS

| | | | |
|---|---|---|---|
| 6,362,234 B1 * | 3/2002 | Hendler | 514/731 |
| 7,060,290 B1 * | 6/2006 | Morimoto et al. | 424/450 |

FOREIGN PATENT DOCUMENTS

| | | |
|---|---|---|
| CN | 101633671 | 1/2010 |
| CN | 101845057 | 9/2010 |
| WO | WO0048572 | 8/2000 |

OTHER PUBLICATIONS

Zaragoza Dorwald, Side Reactions in Organic Synthesis, 2005, WILEY-VCH Verlag GmbH & Co. KGaA, Weinheim, Preface. p. IX.*

* cited by examiner

*Primary Examiner* — Paul A Zucker
(74) *Attorney, Agent, or Firm* — Cesari and McKenna, LLP

(57) ABSTRACT

Phosphate ester compound of hydroxy acid substituted phenyl ester, preparation method and medical use thereof are provided. The title compound is shown in formula (I), in which $Y=C_{1-4}$ straight carbon chain, $M_1$ and/or $M_2$=H, alkali metal ion, protonated amine or protonated amino acid. The compound has good water solubility and high stability in its aqueous solution, and it can release 2,6-diisopropylphenol rapidly under the action of enzymes in vivo, which has the effects of sedation, hypnosis and/or anesthesia. By protecting hydroxyl of 2,6-diisopropylphenol in compound of formula (I), the first-pass metabolic activity of 2,6-diisopropylphenol is reduced, so that the synthetic compound can be used for sedation, hypnosis and/or anesthesia.

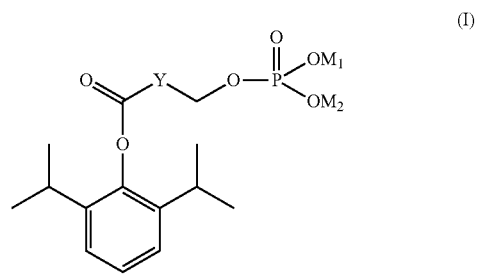

(I)

17 Claims, 2 Drawing Sheets

PHOSPHATE ESTER COMPOUND OF HYDROXY ACID SUBSTITUTED PHENOL ESTER, PREPARATION METHOD AND MEDICAL USE THEREOF

CROSS-REFERENCE TO RELATED APPLICATIONS

This application is the National Stage of International Application No. PCT/CN2010/001601, filed on Oct. 13, 2010, which claims the priority of Chinese Application No. 201010206942.7, filed on Jun. 23, 2010. The contents of both applications are hereby incorporated by reference in their entirety.

FIELD OF THE INVENTION

The present invention relates to a phosphate ester compound of hydroxy acid substituted phenol ester, preparation method and medical use thereof. The compound can be used as a sedative-hypnotic agent and/or anesthetic administered intravenously or non-intravenously.

BACKGROUND OF THE INVENTION

Propofol (chemical name: 2,6-diisopropylphenol) is a sedative-hypnotic agent that has been widely used in clinical practice for induction and maintenance of general anesthesia and for intensive care. Propofol has the characteristics of rapid onset and fast metabolic inactivation and so it has increasingly been used widely in the world since its first clinical report in 1977. As the water solubility of propofol is only 146 mg/L, its clinical formulation is an oil-in-water (O/W) emulsion, in which propofol accounts for 1%; soybean oil, 10%; glycerol, 2.25%; and purified egg yolk lecithin, 1.2%. In the U.S.A, for example, 0.005% disodium edetate is also included as a bacteria growth inhibitor. This formula is a milk-white liquid with a pH value of 7.0, which is slightly viscous, easily injectable, stable at room temperature, and insensitive to light, and is packed in ampoules, under nitrogen gas. However, this preparation still has many disadvantages. For example, as an emulsion form for injection, various stabilizers and solubilizers contained can inevitably cause allergic reactions. Soybean oil and lecithin contained can breed bacteria easily; therefore, it must be prepared under the strict aseptic condition, and it is hard to store when unsealed. Meanwhile, a big oil droplet contained may cause embolism or even serious cardiac adverse effects. Besides, this kind of formulation cannot overcome the disadvantage of 2,6-diisopropylphenol being easily oxidized and deteriorated. All of these disadvantages have limited the use of 2,6-diisopropylphenol to some extent.

Some chemical methods have been reported to overcome those disadvantages of 2,6-diisopropylphenol, which inevitably involved the preparation of some water-soluble prodrugs by modification of the hydroxyl group of 2,6-diisopropylphenol such as propofol phosphates disclosed in WO200213810. But some of those compounds could not rapidly release 2,6-diisopropylphenol in vivo and could not achieve a rapid induction of anesthesia. For another example, the prodrugs disclosed in WO2003059255 could release formaldehyde molecules after hydrolysis, which could cause some adverse effects. For one more example, the propofol succinic acid monoester sodium salt disclosed in WO200213810 is a derivative of 2,6-diisopropylphenol with high water-solubility, but it is unstable in aqueous solution, which also limits the development and application of water-soluble prodrugs of 2,6-diisopropylphenol.

SUMMARY OF THE INVENTION

In view of the above problems, the present invention provides a phosphate ester compound of hydroxy acid substituted phenol ester for the first time; the present invention also provides a preparation method and a medical use of the compound.

The phosphate ester compound of hydroxy acid substituted phenol ester of the present invention is represented by the following structure formula (I):

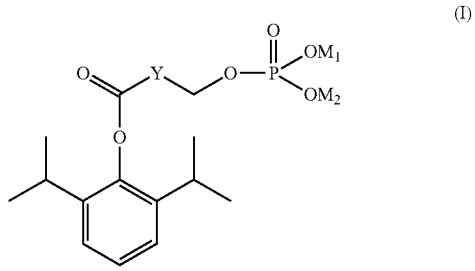

wherein, Y is $C_{1-4}$ straight carbon chain; preferably, the straight carbon chain Y is a saturated carbon chain; more preferably, the straight carbon chain Y is —$CH_2$—$CH_2$— or —$CH_2$—$CH_2$—$CF_{12}$—; $M_1$ and $M_2$ are the same or independently represent hydrogen, alkali metal ion, protonated amino or protonated amino acid.

Besides the simple straight carbon chain forms, the straight carbon chain Y in the compound of the above formula (I) may also be the substituted forms where at least one hydrogen atom of the carbon chain may be substituted with a member of the group consisting of methyl, ethyl, cyclopropyl, hydroxy, sulfydryl, amino or substituted amino group.

The experimental results have shown that as a prodrug of propofol, the compound of formula (I) of the present invention has good water solubility, and its aqueous solution has high stability. When formulated into a pharmaceutically acceptable solution dosage form and administrated intravenously or non-intravenously as a central depressant to produce sedative, hypnotic and/or anesthetic effect on animals or human beings, it can rapidly release phosphate radical under the action of alkaline phosphatases that are widely present in vivo, and further rapidly decompose and release the substituted phenol structure (propofol) to produce sedative, hypnotic and/or anesthetic effect; therefore, the disadvantages of its poor water-solubility and the easy oxidization of its hydroxyl group in the substituted phenol structure could be effectively overcome, the stability of the prodrug in vitro could be enhanced, and the advantages of its being stable in vitro and being rapidly decomposed in vivo could be exhibited. Meanwhile, the phosphate radical, hydroxy acid or the corresponding esterified product released from the compound of formula (I) are harmless to the human body. Accordingly, when used as a central depressant to produce sedative, hypnotic and/or anesthetic effect on animals or human beings through an intravenous or non-intravenous route, the phosphate ester compound of hydroxy acid substituted phenol ester of formula (I) of the present invention has a desirable action and effect.

A typical method of preparing the phosphate ester compound of hydroxy acid substituted phenol ester is provided, comprising the following steps:

1': reacting 2,6-diisopropylphenol (II) as a raw material with dicarboxylic anhydride compound (III) in the presence of a deacidifying agent and 4-dimethylaminopyridine as a catalyst, to form a diacid monoester intermediate (IV); the reaction is performed at the temperatures ranging from room temperature to reflux temperature, or even at a lower temperature below 0° C. After the removal of triethylamine, the residue is added with water and adjusted with a conventional acid, e.g., hydrochloric acid, until the acidic pH point is reached so that the precipitate is formed completely. The precipitate is separated to obtain the diacid monoester intermediate of 2,6-diisopropylphenol (IV). Besides the dianhydride compound (III), 2,6-diisopropylphenol can also be allowed to react with an equimolar amount of diacid compound (III') at the temperatures ranging from 0° C. to room temperature in the presence of an equimolar amount of N,N-dicyclohexylcarbodiimide (DCC) as a condensating agent and a catalytic amount of 4-dimethylaminopyridine. After completion of the reaction, the reactant is filtered to remove precipitate and the filtrate is evaporated to remove the solvent to obtain the diacid monoester intermediate (IV). The resultant crude diacid monoester intermediate (IV) can be further recrystallized with cyclohexane/ethyl acetate or other suitable solvents to obtain the purified intermediate (IV);

2': reacting the intermediate (IV) with sodium borohydride and iodine fully (e.g., until no bubbles occurring, the reaction solution turning to colorless), to obtain the corresponding hydroxy acid substituted phenol ester intermediate compound (V);

3': reacting the intermediate (V) with a sulfonyl halide reagent in the presence of a deacidifying agent to perform sulfonylation reaction, to obtain the corresponding sulfonyl ester intermediate (VI); the reaction being performed at the temperatures ranging from −40° C. to reflux temperature;

4': reacting the sulfonyl ester intermediate (VI) with a halogenated alkali metal salt to obtain a halogenated intermediate (VII); the reaction being performed at the temperatures ranging from room temperature to reflux temperature;

5': reacting the halogenated intermediate (VII) with phosphoric acid in the presence of a tertiary amine compound, e.g., triethylamine or pyridine, to perform phosphate reaction, followed by acidification, and then reacted with a base of alkali metal or an amine or amino acid containing a basic amino group under alkaline conditions to form a salt, to obtain the target compound phosphate ester compound of hydroxy acid substituted phenol ester (I); the above reaction steps: being shown in FIG. 3

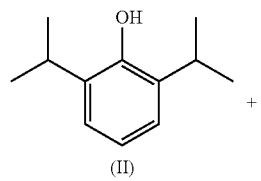

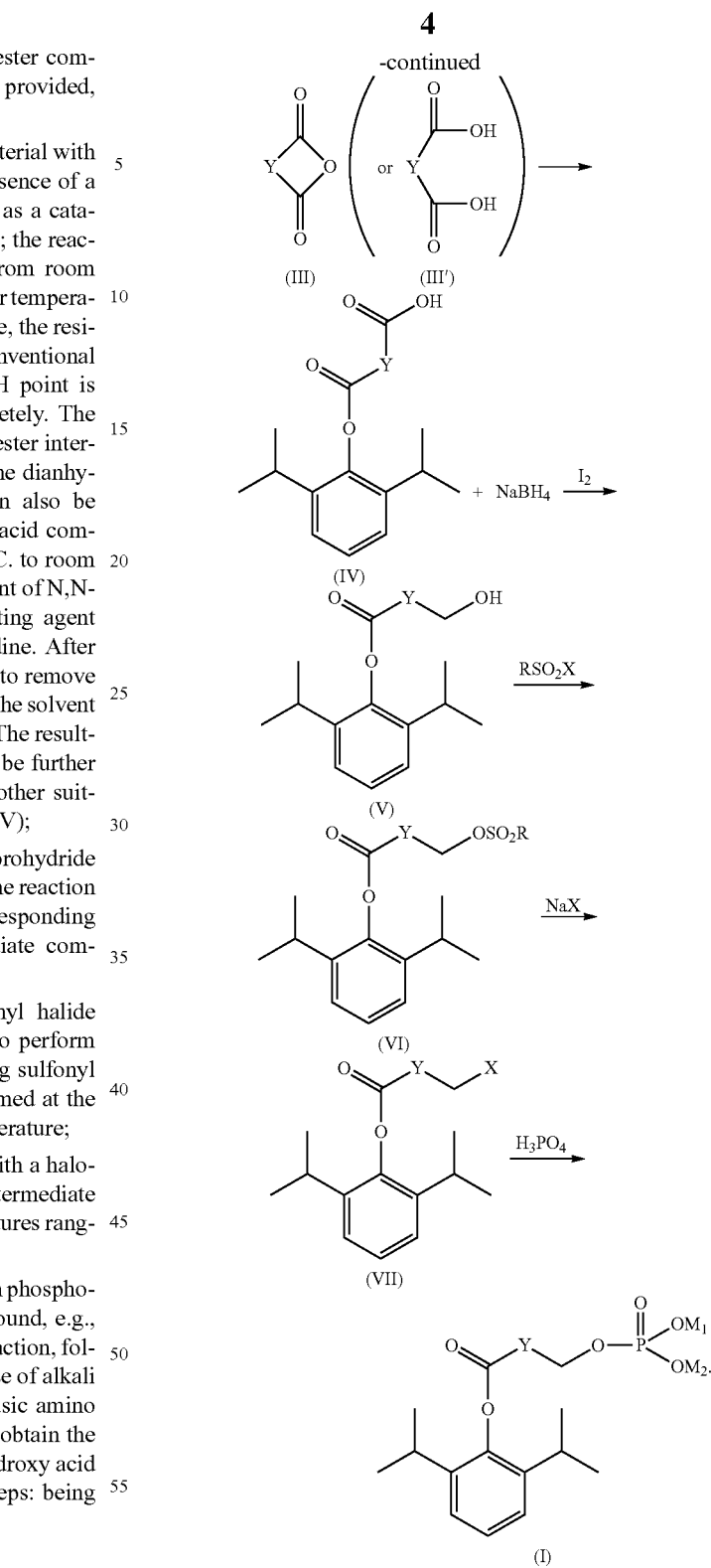

In the reaction route, Y of the diacid compound (III') or the dicarboxylic anhydride compound (III) is $C_1$-$C_4$ straight carbon chain, and preferably is —$CH_2$—$CH_2$— or —$CH_2$—$CH_2$—$CH_2$—. Generally, the sulfonyl halide reagent is p-toluene sulfonyl halide or methyl sulfonyl halide. X is a halogen atom, and preferably is Cl. X' of NaX' is Cl$^-$, Br$^-$ or I$^-$, and preferably is I$^-$. Depending on the base or the compound containing the basic group used in Step 5', $M_1$ and $M_2$ of the target compound (I) can be the corresponding hydrogen, alkali metal ion, protonated amino or protonated amino acid.

Said preparation method can usually be performed in at least one commonly-used organic solvent selected from the group consisting of methylene dichloride, chloroform, carbon tetrachloride, chlorobenzene, benzene, methylbenzene, petroleum ether, cyclohexane, n-hexane, acetonitrile, acetone, dimethylformamide (DMF), dimethyl sulphoxide (DMSO), tetrahydrofuran, diethyl ether, triethylamine or pyridine. Said deacidifying agent in the above preparation method can be selected from pyridine or a tertiary amine compound such as triethylamine.

It could be understood that by preparing the phosphate ester derivative of hydroxy acid ester of 2,6-diisopropylphenol (propofol), which may be further reacted with a base or a molecular containing basic group to form a pharmaceutically acceptable salt, the phosphate ester compound of hydroxy acid substituted phenol ester of formula (I) of the present invention can improve the water solubility of propofol, making the decomposition process faster in vivo, and the stability of the prodrug greater in vitro; thus, it can be used as a central depressant to produce sedative, hypnotic and/or narcotic effect on animals or human beings through an intravenous or non-intravenous route, so that the application scope of the propofol prodrug can be enlarged.

The present invention will be further described in detail in conjunction with the embodiments shown in the drawings and examples; however, it should not be construed as limiting the scope of the present invention to the following examples. Without departing from the technical thought of the present invention, various modifications or changes can be made in accordance with the ordinary skills and the conventional means in the field and should be included in the scope of the present invention.

DETAILED DESCRIPTION OF THE INVENTION

Example 1

Figure 1:
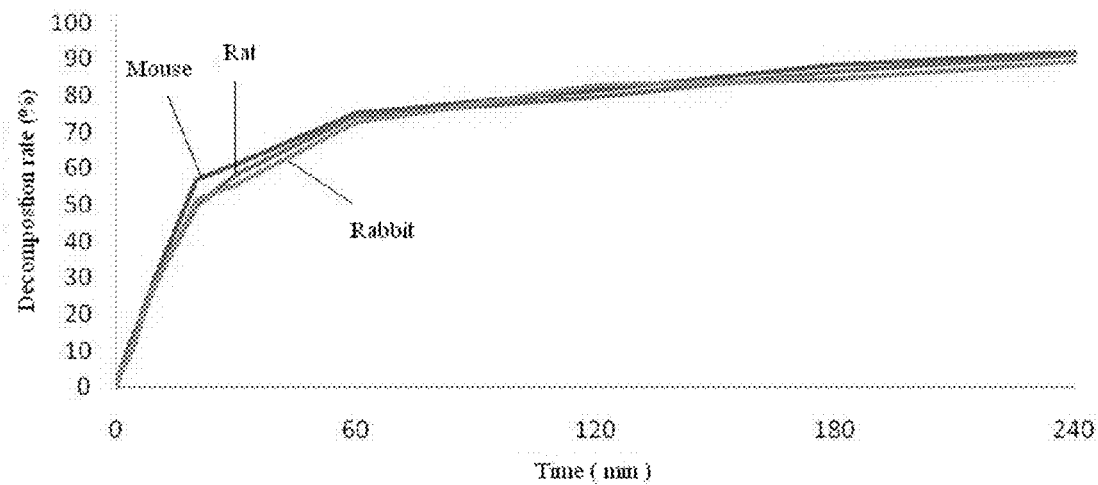
FIG. 1 is an in vitro decomposition curve of propofol hydroxybutyrate phosphate in the plasma.

20 g of propofol (II) was dissolved in 50 ml of triethylamine, added with 14 g of succinyl oxide and 0.02 g of DMAP (4-dimethylamino-pyridine). The mixture was reacted completely for 16 hours under stirring at room temperature, and the reaction solution was evaporated to remove triethylamine. The residue was added into 100 ml of water and adjusted to pH 1 with 6N HCl to produce a great amount of white precipitate. The precipitate was separated and then dried under reduced pressure to give crude propofol succinate monoester (IV), which was recrystallized with cyclohexane/ethyl acetate to obtain 23.5 g of acicular crystals. Yield: 75.4%, mp: 103-104° C.

2.54 g of sodium tetrahydroborate was suspended in 45 ml of anhydrous tetrahydrofuran, cooled to below 5° C., and then slowly added dropwise with 18 g of propofol succinic acid monoester (IV) in tetrahydrofuran, with the temperature maintaining below 5° C. After completion of the dropwise addition, the mixture was stirred under a low temperature for 2 hours until no bubbles occurred, and then added dropwise with 8.28 g of iodine in 70 ml of tetrahydrofuran, with the color of the solution not becoming yellow. After completion of the dropwise addition, the mixture was stirred for 1 hour under the constant temperature. The reaction solution was evaporated to remove tetrahydrofuran, and added with 100 ml of ethyl acetate to produce precipitate. The precipitate was filtered off and the filtrate was washed with 100 ml of saturated sodium bicarbonate solution and 100 ml of water, respectively. The organic layer was separated, dried over anhydrous magnesium sulfate, and then evaporated to remove the solvent ethyl acetate to obtain 16.24 g of propofol ω-hydroxybutyrate intermediate (V) as colorless oil. No impurity was detected by TLC. Yield: 95%.

The above intermediate (V) was dissolved in 40 ml of methylene dichloride, cooled to below 5° C., slowly added dropwise and mixed with 11 g of p-toluenesulfonyl chloride, then slowly added dropwise with 12 g triethylamine. The mixture was reacted for 2 hours under a low temperature, and then reacted overnight at room temperature. The reaction solution was poured into 50 ml of 6N HCl and shaken. The organic layer was separated, washed with water once, and evaporated under reduced pressure to remove the solvent. The residue was recrystallized with cyclohexane to obtain 18.2 g of propofol w-hydroxybutyrate monoester p-toluenesulfonate ester (VI) as white solid. mp: 73-74° C., yield: 70.8%.

7.75 g of the intermediate (VI) was dissolved in 40 ml of DMF and added with 4.9 g of sodium iodide. The mixture was reacted at 50° C. for 1 hour under stirring until no raw material was detected by TLC. The reaction solution was added into 400 ml of water and extracted with 100 ml of ethyl acetate, and the organic layer was separated and evaporated under reduced pressure to remove the solvent to obtain 7.50 g of crude iodinated intermediate (VII).

7.50 g of crude iodinated intermediate (VII) was dissolved in 100 ml of acetonitrile, then added with 9 g of 85% phosphoric acid and 13 g of triethylamine in 50 ml of acetonitrile. The mixture was reacted at 65° C. for 3 hours until no raw material was detected by TLC. The reaction solution was evaporated under reduced pressure to remove the solvent and the residue was mixed with 100 ml of 3N HCl to obtain turbid liquid, which was extracted with 100 ml of methylene dichloride for several times. The organic layers was combined and evaporated under reduced pressure to remove the solvent, to obtain crude propofol w-hydroxybutyrate phosphate ester (I) as soft yellow solid. The crude product was added with sodium hydroxide in methanol to adjust pH to 9, evaporated under reduced pressure to remove methanol, added with 30 ml of ethyl acetate and 15 ml of acetone to produce a great amount of white solid, and then refluxed at 70° C. for 10 minutes, cooled, filtered, evaporated under reduced pressure, to obtain 4.25 g of propofol w-hydroxybutyrate phosphate disodium salt (I) as white crystals.

Structure Detection:

1) NMR spectrometer: BRUKER 400M, using $D_2O$ as a solvent and TMS as an internal standard. δ was expressed in ppm.

$^1$HNMR(δ): 1.06-1.08 (2s, 12H), 1.94-2.01 (m, 2H), 2.78-2.83 (m, 4H), 3.74-3.78 (q, 2H), 7.20-7.26 (m, 3H). Wherein, the multiplet at 3.74-3.78 was the signal of hydrogen on the C atom binding to the phosphate ester group in the molecule.

2) NMR spectrometer: BRUKER 400M, using $D_2O$ as a solvent and TMS as an internal standard. δ was expressed in ppm.

$^{13}$CNMR (δ): 21.94, 23.03, 25.87, 25.94, 27.11, 30.48, 63.15, 124.40, 127.39, 140.85, 144.66, 176.09. Wherein, the signal of the carbon atom binding to the phosphate ester group in the molecule was shown at 63.15, and the signal of carbonyl carbon in the molecule was shown at 176.09.

3) High-resolution mass spectrometric detection: Mass Spectrometer: API 3000 LC-Ms/Ms (ABI, U.S.A.); Ionization Mode: EDI.

Ms$^+$: 389.1100 ($C_{16}H_{24}O_6PNa_2$).

Example 2

20 g of propofol was dissolved in 100 ml of methylene dichloride, added with 13.3 g of succinic acid, 0.02 g of DMAP, and then 23.2 g of DCC. The mixture was reacted for 6 hours under stirring at room temperature, then the reaction solution was filtrated to remove white solid, and the filtrate was washed once with 150 ml of 6N hydrochloric acid. The organic layer was separated and evaporated under reduced pressure to remove the solvent to give crude propofol succinate monoester (IV) as pale yellow solid, which was recrystallized with cyclohexane/ethyl acetate to obtain 26.6 g of white acicular crystals. Yield: 85%, mp: 102-103° C.

The method of preparing propofol w-hydroxybutyrate phosphate ester and/or its disodium salt (I) from propofol succinate monoester intermediate (IV) was similar to that of Example 1.

Example 3

10 g of propofol (II) was dissolved in 50 ml of triethylamine, added with 7 g of glutaric anhydride (III) and 0.01 g of DMAP. The mixture was stirred for 12 hours at room temperature, and the reaction solution was evaporated under reduced pressure to remove excessive triethylamine. The residue was added into 100 ml of water and adjusted to pH 1 with 6N HCl to produce a great amount of white precipitate. The precipitate was separated and then dried under reduced pressure to give crude product, which was recrystallized with cyclohexane/ethyl acetate to obtain 10.8 g of propofol glutarate monoester intermediate (IV) as white flaky crystals. Yield: 65.9%, mp: 53-54° C.

2.54 g of sodium tetrahydroborate was suspended in 45 ml of anhydrous tetrahydrofuran, cooled to below 5° C., and then slowly added dropwise with 19 g of propofol glutarate monoester intermediate (IV) in 60 ml of tetrahydrofuran, with the temperature maintaining below 5° C. After completion of the dropwise addition, the mixture was stirred at a low temperature for 2 hours until no bubbles occurred, and then added dropwise with 8.28 g of iodine in 70 ml of tetrahydrofuran, with the color of the solution not becoming yellow. After completion of the dropwise addition, the mixture was stirred for 1 hour under the constant temperature. The reaction solution was evaporated to remove tetrahydrofuran, and added with 100 ml of ethyl acetate to produce precipitate. The precipitate was filtered off and the filtrate was washed once with 100 ml of saturated sodium bicarbonate solution and 100 ml of water, respectively. The organic layer was separated, dried over anhydrous magnesium sulfate overnight, filtrated to remove the drying agent and then evaporated to remove ethyl acetate to obtain 16.9 g of propofol w-hydroxyvalerate intermediate (V) as colorless oil. No impurity was detected by TLC. Yield: 93%.

The above intermediate (V) was dissolved in 40 ml of methylene dichloride, cooled to below 5° C., slowly added dropwise and mixed with 11 g of p-toluenesulfonate chloride, then slowly added dropwise with 12 g triethylamine. The mixture was reacted for 2 hours at this low temperature, and then reacted overnight at room temperature. The reaction solution was poured into 50 ml of 6N HCl and shaken. The organic layer was separated, washed with water once, and evaporated under reduced pressure to remove the solvent. The residue was recrystallized with cyclohexane to obtain 19 g of propofol w-hydroxyvalerate p-toluenesulfonate ester intermediate (VI) as colorless oil. mp: 64-65° C., yield: 72.24%.

8 g of the above p-toluenesulfonate ester intermediate (VI) was dissolved in 40 ml of DMF and added with 4.9 g of sodium iodide. The mixture was reacted at 50° C. for 1 hour under stirring until no raw material was detected by TLC. The reaction solution was added into 400 ml of water and extracted with 100 ml of ethyl acetate, and the organic layer was separated and evaporated under reduced pressure to remove the solvent to obtain 8.1 g of crude iodinated intermediate (VII).

The above crude iodinated intermediate (VII) was dissolved in 100 ml of acetonitrile, then added with 9 g of 85% phosphoric acid and 13 g of triethylamine in 50 ml of acetonitrile. The mixture was reacted at 65° C. for 3 hours until no raw material was detected by TLC. The reaction solution was evaporated under reduced pressure to remove the solvent, and the residue was mixed with 100 ml of 3N HCl to obtain turbid liquid, which was extracted with 100 ml of methylene dichloride for several times. The organic layers were combined and evaporated under reduced pressure to remove the solvent, to obtain crude propofol w-hydroxyvalerate phosphate ester (I) as soft yellow solid. The crude product was added with sodium hydroxide in methanol to adjust pH to 9, evaporated under reduced pressure to remove methanol, added with 30 ml of ethyl acetate and 15 ml of acetone to produce a great amount of white solid, and then refluxed at 70° C. for 10 minutes, cooled, filtered, evaporated under reduced pressure, to obtain 2.5 g of propofol w-hydroxyvalerate phosphate disodium salt (I) as white crystals.

Structure Detection:

1) NMR spectrometer: BRUKER 400M, using $D_2O$ as a solvent and TMS as an internal standard. δ was expressed in ppm.

$^1$HNMR(δ): 1.07-1.08 (2s, 12H), 1.63-1.66 (m, 2H), 1.77-1.78 (m, 2H), 2.73-2.75 (m, 2H), 2.80-2.83 (m, 2H), 3.71-3.74 (m, 2H), 7.21-7.25 (m, 3H). Wherein, the multiplet at 3.71-3.74 was the signal of hydrogen on the C atom binding to the phosphate ester group in the molecule.

2) NMR spectrometer: BRUKER 400M, using $D_2O$ as a solvent and TMS as an internal standard. δ was expressed in ppm.

$^{13}$CNMR(δ): 20.98, 21.97, 23.01, 23.37, 27.22, 29.91, 63.81, 124.51, 127.47, 140.99, 144.74, 176.38. Wherein, the signal of the carbon atom binding to the phosphate ester group in the molecule was shown at 63.81, and the signal of carbonyl carbon in the molecule was shown at 176.38.

3) High-resolution mass spectrometric detection: Mass Spectrometer: API 3000 LC-Ms/Ms (ABI, U.S.A.); Ionization Mode: EDI.

Ms$^+$: 403.1256 ($C_{17}H_{25}O_6PNa_2$)

Example 4

10 g of propofol was dissolved in 50 ml of methylene dichloride, added with 7.4 g of glutaric acid, 0.01 g of DMAP, and then 11.6 g of DCC. The mixture was reacted for 6 hours under stirring at room temperature, then the reaction solution was filtrated to remove white solid and the filtrate was washed once with 80 ml of 6N HCl. The organic layer was separated and evaporated under reduced pressure to remove the solvent to give pale yellow solid, which was recrystallized with cyclohexane/ethyl acetate to obtain 9 g of propofol glutarate monoester intermediate (IV) as white acicular crystals. Yield: 54.9%, mp: 53-54° C.

The method of preparing propofol w-hydroxyvalerate phosphate ester and/or its disodium salt (I) from propofol glutarate monoester intermediate (IV) was similar to that of Example 3.

Example 5

Three parallel solutions of propofol w-hydroxybutyrate phosphate disodium salt (I) of Example 1 with a concentration of 10 mg/ml were prepared, added into and mixed with the mouse, rat or rabbit plasma, which was pre-placed in water bath (37° C.), respectively. 100 µl of the drug-containing plasma was taken at 0 min, 1 min, 3 min, 5 min, 7 min, 10 min, 20 min, 30 min, 1 h, 2 h, 3 h and 4 h, respectively, and the concentrations of the active metabolite propofol were determined by the HPLC method. The results shown in FIG. 1 have indicated that the phosphate sodium salt of propofol hydroxybutyrate in the plasma can be rapidly decomposed into the active compound propofol (II).

Example 6

Figure 2:
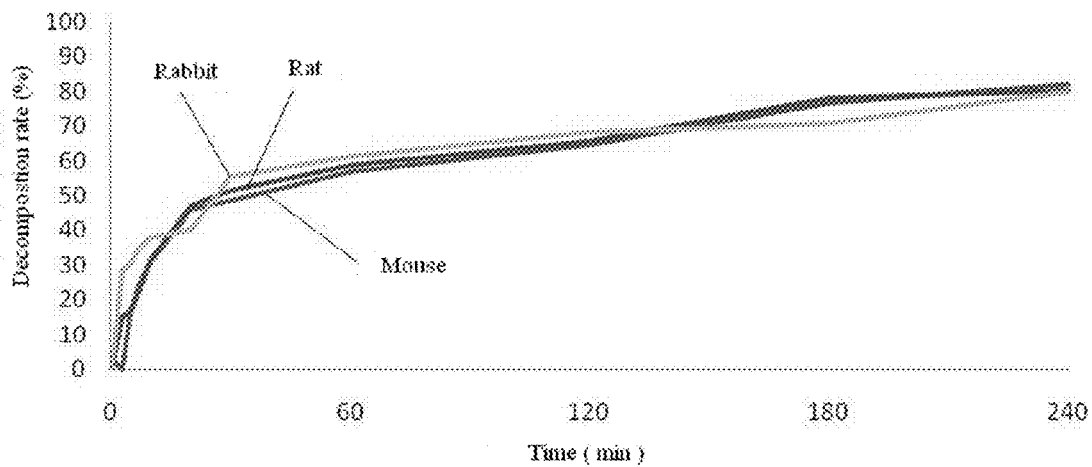
FIG. 2 is an in vitro decomposition curve of propofol hydroxyvalerate phosphate in the plasma.
Figure 3:
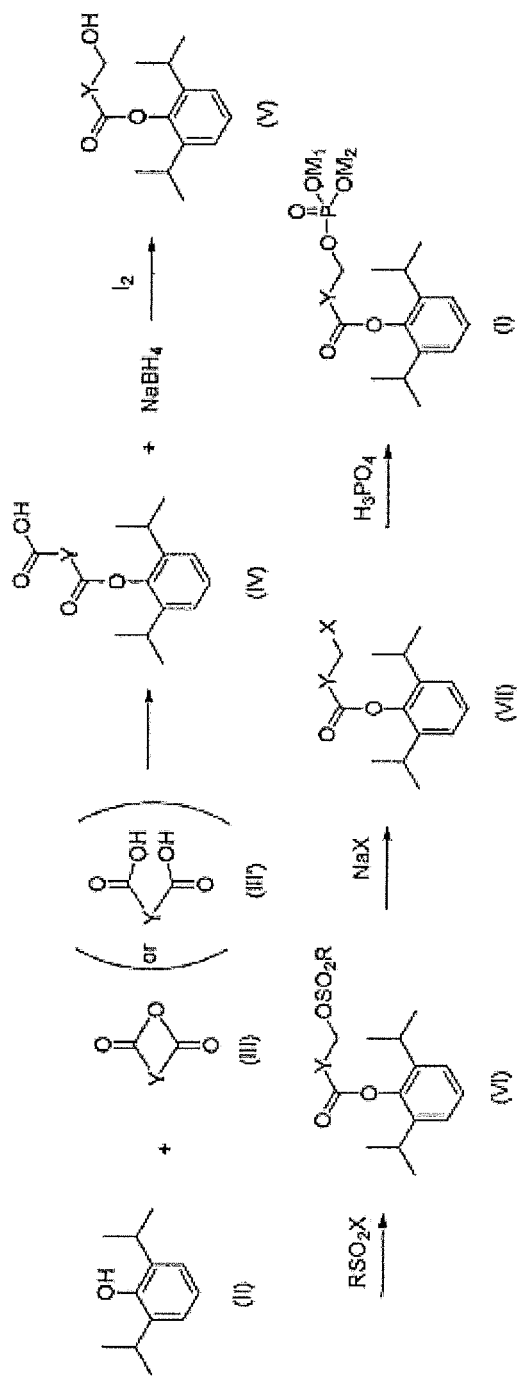
FIG. 3 is a general synthetic route for preparing a phosphate ester compound of hydroxy acid substituted phenol ester.

Three parallel solutions of propofol ω-hydroxyvalerate phosphate disodium salt (I) of example 3 with a concentration of 10 mg/ml were prepared, added into and mixed with the mouse, rat or rabbit plasma, which was pre-placed in water bath (37° C.), respectively. 100 µl of the drug-containing plasma was taken at 0 min, 1 min, 3 min, 5 min, 7 min, 10 min, 20 min, 30 min, 1 h, 2 h, 3 h and 4 h, respectively, and the concentrations of the active metabolite propofol were determined by the HPLC method. The results shown in FIG. 2 have indicated that the phosphate sodium salt of propofol hydroxyvalerate in the plasma can be rapidly decomposed into the active compound propofol (II).

Example 7

60 Kunming mice with half males and half females were randomly divided into the drug test group (propofol ω-hydroxybutyrate phosphate disodium salt for injection as in Example 1 of the present invention) (n=30) and the Diprivan™ control group (positive control drug Diprivan™) (n=30). Median effective doses ($ED_{50}$) of propofol hydroxybutyrate phosphate disodium salt and Diprivan™ were determined by the up-and-down method. In the test, the mice were injected with the drugs through the tail veins, with the disappearance of the forepaw righting reflex (FRR) of the mice as a judgment index of the end point of anesthesia; the recovery of FRR of the mice as an index of recovery from anesthesia. The results have shown that $ED_{50}$ of the propofol ω-hydroxybutyrate phosphate disodium salt group of the present invention was 130 mg/kg, with 95% confidence interval of 125~140 mg/kg. $ED_{50}$ of the Diprivan™ control group was 5.8 mg/kg, with 95% confidence interval of 5.3~7.8 mg/kg. During the determination of $ED_{50}$, it was observed that the disappearance time of FRR in the propofol hydroxybutyrate phosphate disodium salt group was 150.6±42.1 seconds and the recovery time was 480.6±124.3 seconds. The onset time was significantly longer than that of the Diprivan™ control group (onset time, 21±2 seconds; recovery time, 270.6±116.2 seconds).

The results have shown that propofol hydroxybutyrate phosphate disodium salt of the present invention has a definite and reversible anesthetic effect.

Example 8

60 Kunming mice with half males and half females were randomly divided into the drug test group (propofol w-hydroxyvalerate phosphate disodium salt for injection as in Example 3 of the present invention) (n=30) and the Diprivan™ control group (positive control drug Diprivan™) (n=30). Median effective doses ($ED_{50}$) of propofol hydroxyvalerate phosphate disodium salt and Diprivan™ were determined by the up-and-down method. In the test, the mice were injected with the drugs through the tail veins, with the disappearance of the forepaw righting reflex (FRR) of the mice as a judgment index of the end point of anesthesia; the recovery of FRR of the mice as an index of recovery from anesthesia. The results have shown that $ED_{50}$ of the propofol hydroxyvalerate phosphate disodium salt group was 152 mg/kg, with 95% confidence interval of 131~164 mg/kg, and $ED_{50}$ of the Diprivan™ control group was 5.9 mg/kg, with 95% confidence interval of 5.1~7.9 mg/kg. During the determination of $ED_{50}$, it was observed that the disappearance time of FRR in the propofol hydroxyvalerate phosphate disodium salt group was 180.8±45.6 seconds, and the recovery time was 500.1±114.6 seconds. The onset time was significantly longer than that of the Diprivan™ control group (onset time, 19±3 seconds; recovery time, 260.2±121.6 seconds). The results have shown that propofol hydroxyvalerate phosphate disodium salt of the present invention also has a definite and reversible anesthetic effect.

INDUSTRIAL APPLICABILITY

The present invention provides a phosphate ester derivative of hydroxy acid ester of propofol, which can be further reacted with a base or a molecular containing basic group to form a pharmaceutically acceptable salt. The compound of the present invention can improve water solubility of propofol, decompose faster in vivo, and increase stability of the prodrug in vitro; therefore, it can be used as a central depressant to produce sedative, hypnotic and/or narcotic effect on animals or human beings through an intravenous or non-intravenous route, the application scope of the propofol prodrug can be enlarged, the positive sense and good prospects can be exhibited; therefore, it is suitable for the industrial applications.

What is claimed is:
1. A phosphate ester compound of hydroxy acid substituted phenol ester represented by the following structure formula (I):

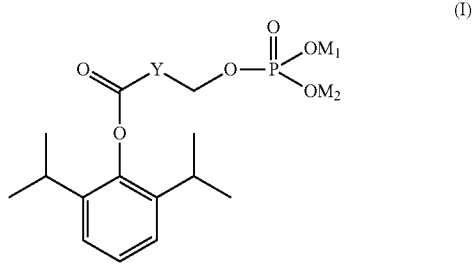

wherein Y is a $C_{1-4}$ straight saturated carbon chain optionally substituted with methyl, ethyl, cyclopropyl, hydroxy, sulfhydryl, amino, or a substituted amino group, $M_1$ and $M_2$ are the same or independently represent hydrogen, alkali metal ion, protonated amino or protonated amino acid.

2. The compound of claim 1, wherein said straight saturated carbon chain Y is —$CH_2$—$CH_2$— or —$CH_2$—$CH_2$—$CH_2$—.

3. The compound of claim 1, wherein the straight saturated carbon chain Y is substituted with methyl, ethyl, cyclopropyl, hydroxy, sulfhydryl, amino, or a substituted amino group.

4. A method of preparing the phosphate ester compound of hydroxy acid substituted phenol ester of claim 1, comprising the steps of:
reacting 2,6-diisopropylphenol (II) as a raw material with a dicarboxylic anhydride compound (III) in the presence of a deacidifying agent and 4-dimethylaminopyridine as a catalyst, to form a diacid monoester intermediate (IV); or reacting 2,6-diisopropylphenol (II) with a diacid compound (III') in the presence of N,N-dicyclohexylcarbodiimide as a condensating agent and a catalytic amount of 4-dimethylaminopyridine, to form the diacid monoester intermediate (IV);
reacting the diacid monoester intermediate (IV) with sodium borohydride and iodine fully to obtain a hydroxy acid substituted phenol ester intermediate (V);
reacting the hydroxy acid substituted phenol ester intermediate (V) with a sulfonyl halide reagent in the presence of a deacidifying agent to perform sulfonylation reaction to obtain a sulfonyl ester intermediate (VI);
reacting the sulfonyl ester intermediate (VI) with a halogenated alkali metal salt to obtain a halogenated intermediate (VII); and
reacting the halogenated intermediate (VII) with phosphoric acid in the presence of a tertiary amine compound including triethylamine or pyridine to perform esterification reaction followed by acidification, and then reacting with a base of alkali metal or an amine or amino acid containing basic amino group to form a salt, to obtain the hydroxy acid substituted phenol ester compound of formula (I),
wherein the diacid compound (III') is

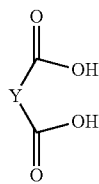

and
the dicarboxylic anhydride compound (III) is

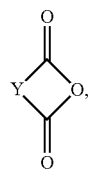

in which Y is a $C_1$-$C_4$ straight saturated carbon chain optionally substituted with methyl, ethyl, cyclopropyl, hydroxy, sulfhydryl, amino, or a substituted amino group; said sulfonyl halide reagent is p-toluene sulfonyl halide or methyl sulfonyl halide; and $M_1$ and $M_2$ of the target compound (I) are selected from hydrogen, alkali metal ion, protonated amino and protonated amino acid.

5. The preparation method of claim 4, wherein said deacidifying agent is pyridine or a tertiary amine compound.

6. The preparation method of claim 5, wherein said preparation method is performed in at least one organic solvent selected from the group consisting of methylene dichloride, chloroform, carbon tetrachloride, chlorobenzene, benzene, methylbenzene, petroleum ether, cyclohexane, n-hexane, acetonitrile, acetone, DMF, DMSO, tetrahydrofuran, diethyl ether, triethylamine and pyridine.

7. The preparation method of claim 4, wherein Y of the corresponding diacid compound (III') or dicarboxylic anhydride compound (III) is —$CH_2$—$CH_2$— or —$CH_2$—$CH_2$—$CH_2$—.

8. A method for producing a sedative effect, a hypnotic effect, and/or an anesthetic effect comprising administering to a subject in need thereof an effective amount of the phosphate ester compound of hydroxy acid substituted phenol ester of claim 1 through an intravenous or non-intravenous route.

9. The compound of claim 2, wherein the straight saturated carbon chain Y is substituted with methyl, ethyl, cyclopropyl, hydroxy, sulfhydryl, amino, or a substituted amino group.

10. A method of preparing the phosphate ester compound of hydroxy acid substituted phenol ester of claim 2, comprising the steps of:
reacting 2,6-diisopropylphenol (II) as a raw material with a dicarboxylic anhydride compound (III) in the presence of a deacidifying agent and 4-dimethylaminopyridine as a catalyst, to form a diacid monoester intermediate (IV); or reacting 2,6-diisopropylphenol (II) with a diacid compound (III') in the presence of N,N-dicyclohexylcarbodiimide as a condensating agent and a catalytic amount of 4-dimethylaminopyridine, to form the diacid monoester intermediate (IV);
reacting the diacid monoester intermediate (IV) with sodium borohydride and iodine fully to obtain a hydroxy acid substituted phenol ester intermediate (V);
reacting the hydroxy acid substituted phenol ester intermediate (V) with a sulfonyl halide reagent in the presence of a deacidifying agent to perform sulfonylation reaction to obtain a sulfonyl ester intermediate (VI);
reacting the sulfonyl ester intermediate (VI) with a halogenated alkali metal salt to obtain a halogenated intermediate (VII); and
reacting the halogenated intermediate (VII) with phosphoric acid in the presence of a tertiary amine compound including triethylamine or pyridine to perform esterification reaction followed by acidification, and then reacting with a base of alkali metal or an amine or amino acid containing basic amino group to form a salt, to obtain the hydroxy acid substituted phenol ester compound of formula (I), wherein the diacid compound (III') is

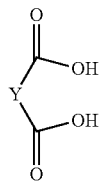

and
the dicarboxylic anhydride compound (III) is

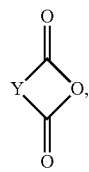

in which Y is a $C_1$-$C_4$ straight saturated carbon chain optionally substituted with methyl, ethyl, cyclopropyl, hydroxy, sulfhydryl, amino, or a substituted amino group; said sulfonyl halide reagent is p-toluene sulfonyl halide or methyl sulfonyl halide; and $M_1$ and $M_2$ of the target compound (I) are selected from hydrogen, alkali metal ion, protonated amino and protonated amino acid.

11. A method of preparing the phosphate ester compound of hydroxy acid substituted phenol ester of claim 3, comprising the steps of:

reacting 2,6-diisopropylphenol (II) as a raw material with a dicarboxylic anhydride compound (III) in the presence of a deacidifying agent and 4-dimethylaminopyridine as a catalyst, to form a diacid monoester intermediate (IV); or reacting 2,6-diisopropylphenol (II) with a diacid compound (III') in the presence of N,N-dicyclohexylcarbodiimide as a condensating agent and a catalytic amount of 4-dimethylaminopyridine, to form the diacid monoester intermediate (IV);

reacting the diacid monoester intermediate (IV) with sodium borohydride and iodine fully to obtain a hydroxy acid substituted phenol ester intermediate (V);

reacting the hydroxy acid substituted phenol ester intermediate (V) with a sulfonyl halide reagent in the presence of a deacidifying agent to perform sulfonylation reaction to obtain a sulfonyl ester intermediate (VI);

reacting the sulfonyl ester intermediate (VI) with a halogenated alkali metal salt to obtain a halogenated intermediate (VII); and reacting the halogenated intermediate (VII) with phosphoric acid in the presence of a tertiary amine compound including triethylamine or pyridine to perform esterification reaction followed by acidification, and then reacting with a base of alkali metal or an amine or amino acid containing basic amino group to form a salt, to obtain the hydroxy acid substituted phenol ester compound of formula (I), wherein the diacid compound (III') is

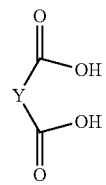

and
the dicarboxylic anhydride compound (III) is

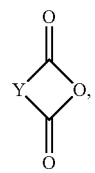

in which Y is a $C_1$-$C_4$ straight saturated carbon chain optionally substituted with methyl, ethyl, cyclopropyl, hydroxy, sulfhydryl, amino, or a substituted amino group; said sulfonyl halide reagent is p-toluene sulfonyl halide or methyl sulfonyl halide; and $M_1$ and $M_2$ of the target compound (I) are selected from hydrogen, alkali metal ion, protonated amino and protonated amino acid.

12. A method of preparing the phosphate ester compound of hydroxy acid substituted phenol ester of claim 9, comprising the steps of:

reacting 2,6-diisopropylphenol (II) as a raw material with a dicarboxylic anhydride compound (III) in the presence of a deacidifying agent and 4-dimethylaminopyridine as a catalyst, to form a diacid monoester intermediate (IV); or reacting 2,6-diisopropylphenol (II) with a diacid compound (III') in the presence of N,N-dicyclohexylcarbodiimide as a condensating agent and a catalytic amount of 4-dimethylaminopyridine, to form the diacid monoester intermediate (IV);

reacting the diacid monoester intermediate (IV) with sodium borohydride and iodine fully to obtain a hydroxy acid substituted phenol ester intermediate (V);

reacting the hydroxy acid substituted phenol ester intermediate (V) with a sulfonyl halide reagent in the presence of a deacidifying agent to perform sulfonylation reaction to obtain a sulfonyl ester intermediate (VI);

reacting the sulfonyl ester intermediate (VI) with a halogenated alkali metal salt to obtain a halogenated intermediate (VII); and reacting the halogenated intermediate (VII) with phosphoric acid in the presence of a tertiary amine compound including triethylamine or pyridine to perform esterification reaction followed by acidification, and then reacting with a base of alkali metal or an amine or amino acid containing basic amino group to form a salt, to obtain the hydroxy acid substituted phenol ester compound of formula (I), wherein the diacid compound (III') is

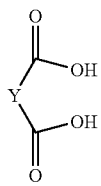

and
the dicarboxylic anhydride compound (III) is

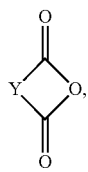

in which Y is a $C_1$-$C_4$ straight saturated carbon chain optionally substituted with methyl, ethyl, cyclopropyl, hydroxy, sulfhydryl, amino, or a substituted amino group; said sulfonyl halide reagent is p-toluene sulfonyl halide or methyl sulfonyl halide; and $M_1$ and $M_2$ of the target compound (I) are selected from hydrogen, alkali metal ion, protonated amino and protonated amino acid.

13. The preparation method of claim 10, wherein said deacidifying agent is pyridine or a tertiary amine compound.

14. The preparation method of claim 11, wherein said deacidifying agent is pyridine or a tertiary amine compound.

15. The preparation method of claim 5, wherein said deacidifying agent is pyridine or triethylamine.

16. The preparation method of claim 13, wherein said deacidifying agent is pyridine or triethylamine.

17. The preparation method of claim 14, wherein said deacidifying agent is pyridine or triethylamine.

* * * * *